(12) United States Patent
Otsuka et al.

(10) Patent No.: US 10,835,637 B2
(45) Date of Patent: Nov. 17, 2020

(54) BIODEGRADABLE INJECTABLE GEL

(71) Applicants: 3-D Matrix, Ltd., Tokyo (JP); Tokyo University of Science Foundation, Tokyo (JP)

(72) Inventors: Hidenori Otsuka, Tokyo (JP); Daisuke Matsukuma, Tokyo (JP); Noriaki Matsuda, Tokyo (JP)

(73) Assignees: 3-D Matrix, Ltd. (Tokyo, Japan), Tokyo (JP); Tokyo University of Science Foundation, Tokyo (JP)

( * ) Notice: Subject to any disclaimer, the term of this patent is extended or adjusted under 35 U.S.C. 154(b) by 0 days.

(21) Appl. No.: 15/754,393

(22) PCT Filed: Aug. 23, 2016

(86) PCT No.: PCT/JP2016/074558
§ 371 (c)(1),
(2) Date: Feb. 22, 2018

(87) PCT Pub. No.: WO2017/033941
PCT Pub. Date: Mar. 2, 2017

(65) Prior Publication Data
US 2018/0250435 A1 Sep. 6, 2018

(30) Foreign Application Priority Data
Aug. 24, 2015 (JP) ................. 2015-165204

(51) Int. Cl.
| | | |
|---|---|---|
| *A61K 9/00* | (2006.01) |
| *A61L 27/52* | (2006.01) |
| *A61L 27/58* | (2006.01) |
| *A61L 27/18* | (2006.01) |
| *C08G 63/664* | (2006.01) |
| *A61L 31/14* | (2006.01) |
| *A61L 29/14* | (2006.01) |
| *A61L 31/10* | (2006.01) |
| *A61L 29/08* | (2006.01) |
| *C08J 3/075* | (2006.01) |
| *C08J 3/24* | (2006.01) |
| *C08K 5/3415* | (2006.01) |
| *C08L 5/08* | (2006.01) |
| *C08L 67/04* | (2006.01) |
| *C08L 71/02* | (2006.01) |

(52) U.S. Cl.
CPC ............. *A61L 27/18* (2013.01); *A61L 27/52* (2013.01); *A61L 27/58* (2013.01); *A61L 29/085* (2013.01); *A61L 29/145* (2013.01); *A61L 29/148* (2013.01); *A61L 31/10* (2013.01); *A61L 31/145* (2013.01); *A61L 31/148* (2013.01); *C08G 63/664* (2013.01); *C08J 3/075* (2013.01); *C08J 3/246* (2013.01); *C08K 5/3415* (2013.01); *C08L 5/08* (2013.01); *C08L 67/04* (2013.01); *C08L 71/02* (2013.01); *A61L 2400/06* (2013.01); *A61L 2430/06* (2013.01); *C08J 2305/08* (2013.01); *C08J 2467/04* (2013.01); *C08L 2203/02* (2013.01)

(58) Field of Classification Search
CPC ....... A61K 9/0019; A61L 27/18; A61L 27/58; A61L 2400/06; A61L 27/52; A61L 31/14; C08J 3/075
USPC ........................................ 530/300
See application file for complete search history.

(56) References Cited

U.S. PATENT DOCUMENTS

| | | |
|---|---|---|
| 8,022,178 B2 | 9/2011 | Horii |
| 9,707,322 B2 | 7/2017 | Nukavarapu |

FOREIGN PATENT DOCUMENTS

| | | |
|---|---|---|
| JP | 11-513985 A | 11/1999 |
| JP | 2001-513368 A | 9/2001 |
| JP | 2001-517603 A | 10/2001 |
| JP | 2004-167229 A | 6/2004 |
| JP | 2006-506335 A | 2/2006 |
| JP | 2007-512094 A | 5/2007 |
| JP | 2010-144178 A | 7/2010 |
| JP | 2001-517603 A | 10/2010 |
| JP | 2011-012042 A | 1/2011 |
| JP | 2011-513985 A | 4/2011 |
| JP | 2013-505336 A | 2/2013 |
| JP | 2015-108160 A | 6/2015 |
| KR | 2002-0027747 A | 4/2002 |
| KR | 10-2013-0110776 A | 10/2013 |
| KR | 10-2013-0110777 A | 10/2013 |
| WO | 09-157368 A | 6/1997 |
| WO | 2014/044704 A1 | 3/2014 |
| WO | 2014/133027 A1 | 9/2014 |

OTHER PUBLICATIONS

Li et al., Langmuir 2007, 23, 2778-2783. (Year: 2007).*
International Search Report and Written Opinion dated Nov. 8, 2016, for Application No. PCT/JP2016/074558.
International Search Report and Written Opinion for Application No. PCT/JP2015/073745, dated Nov. 10, 2015 (w Engl. translation of Written Opinion 5 pages, with Engl. translation of Search Report, 2 pgs.).

(Continued)

*Primary Examiner* — James H Alstrum-Acevedo
*Assistant Examiner* — Kaipeen E Yang
(74) *Attorney, Agent, or Firm* — IP Supra, PLLC; Constantine M. Linnik; Robert Kelley Roth

(57) ABSTRACT

The present invention relates to a triblock copolymer having a polyethylene glycol-poly(D,L-lactide)-polyethylene glycol skeleton.

3 Claims, 13 Drawing Sheets
Specification includes a Sequence Listing.

(56) References Cited

OTHER PUBLICATIONS

Matsukuma, D., et al., "3D Scaffold," CSJ: The Chemical Society of Japan Dai 93 Shunki Nekai 2013 Nen Koen Yokoshu III, 2013, p. 845 (Abstract only).
Zhang, H., et al., "Mechanistic Study of Self-Assembling Peptide RADA 16-1 in Formation of Nanofibers and Hydrogels," J. Nanotech. Eng. Med., 2010, v.1 pp. 11007.1-11007.6.
Jiang et al, "Click hydrogels, microgels and nanogels: Emerging platforms for drug delivery and tissue engineering," Biomaterials, 2014m, 35: 4969-4985.
Sahiner et al, "Microgel, nanogel and hydrogel-hydrogel semi-IPN composites for biomedical applications: synthesis and characterization," Colloid Polym. Sci, 2006, 284: 1121-1129.
International Publication No. WO 2014/133027, (Sep. 4, 2014). (See English equivalent abstract).

\* cited by examiner

THP-PEG-OH

THP-PEG-PLA-OH

THP-PEG-PLA-PEG-THP

□ PEG 5k (-)
□ PEG-PLA-PEG (-)
■ PEG 5k (+)
■ PEG-PLA-PEG (+)

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: synthesized peptide

<400> SEQUENCE: 1

Arg Ala Asp Ala Arg Ala Asp Ala Arg Ala Asp Ala Arg Ala Asp Ala
1               5                   10                  15

BIODEGRADABLE INJECTABLE GEL

This application is a US national stage application of international patent application PCT/JP2016/074558 filed on Aug. 23, 2016, which claims priority to Japanese patent application 2015-165204 filed on Aug. 24, 2015, which is hereby incorporated by reference.

TECHNICAL FIELD

The present invention relates to a biodegradable injectable gel composed of a PEG-PLA-PEG triblock copolymer, a self-assembling peptide and chitosan.

BACKGROUND ART

In the field of regenerative medicine, hydrogels enabling precise control of the physical properties thereof are attracting attention for use as scaffolds providing an effective site for cell proliferation and differentiation. We have previously found that an interpenetrating polymer network (IPN) type of injectable gel (chitosan/PEG/RADA16), composed of a self-assembling peptide gel (RADA16), functioning as a pseudo extracellular matrix, and a covalently bonded gel (chitosan/PEG) functioning as a mechanical support, can serve as a useful scaffold for regeneration of cartilage tissue. A peptide fiber network contained in the gel contributes to enhanced cell function, and as a result, was confirmed to promote superior regeneration of cartilage tissue in vivo.

On the other hand, following induction of regeneration of body tissue, it is preferable that the scaffold be degraded and eliminated and then replaced with normal tissue. Since covalently-bonded chitosan/PEG gel has poor degradability, it was difficult to control degradation of the scaffold following regeneration of body tissue.

DISCLOSURE OF THE INVENTION

Problems to be Solved by the Invention

The present invention provides a biodegradable injectable gel.

Means for Solving the Problems

The present invention provides a biodegradable injectable gel (chitosan/PEG-PLA-PEG/RADA16) that uses a PEG-PLA-PEG triblock copolymer (FIG. 1) introduced with poly(D,L-lactide) (PLA).

Namely, the present invention relates to that indicated below.

[1] A triblock copolymer having a polyethylene glycol-poly(D,L-lactide)-polyethylene glycol skeleton.

[2] The triblock copolymer described in [1], containing a repeating unit represented by formula I:

[Chemical Formula 1]

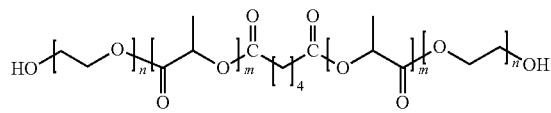

(I)

(wherein, n represents a degree of polymerization and is preferably within the range of 10 to 1000, and m represents a degree of polymerization and is preferably within the range of 1 to 100).

[3] A biodegradable injectable gel containing the triblock copolymer described in [1] or [2], chitosan, and a self-assembling peptide.

[4] The biodegradable injectable gel described in [3], wherein the self-assembling peptide is $(RADA)_4$.

[5] A method for producing a triblock copolymer having a polyethylene glycol-poly(D,L-lactide)-polyethylene glycol skeleton, including:

a step for reacting the following:

[Chemical Formula 2]

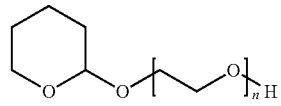

(wherein, n represents a degree of polymerization and is within the range of 10 to 1000), with L-lactide to obtain

[Chemical Formula 3]

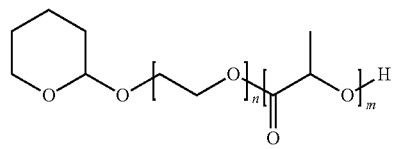

(wherein, m represents a degree of polymerization and is within the range of 1 to 100), a step for reacting the resulting

[Chemical Formula 4]

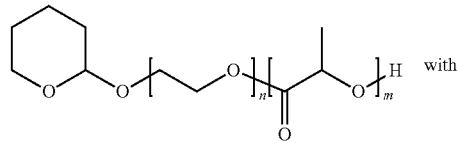 with

[Chemical Formula 5]

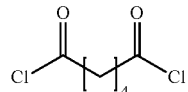

to obtain

[Chemical Formula 6]

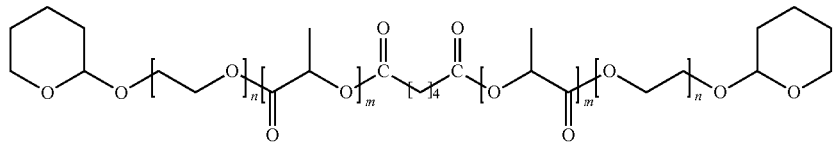

followed by de-protecting the resulting

[Chemical Formula 7]

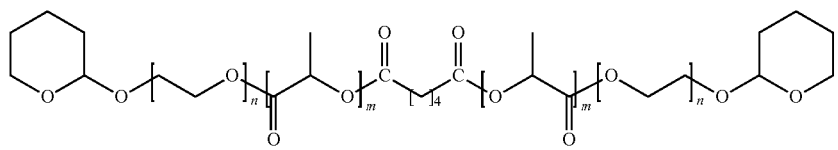

to obtain

[Chemical Formula 8]

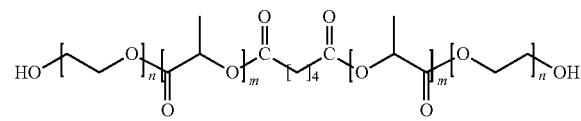

and, a step for reacting the resulting

[Chemical Formula 9]

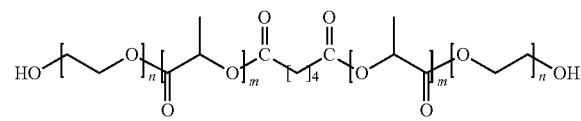

with di(N-succinimidyl)carbonate to obtain

[Chemical Formula 10]

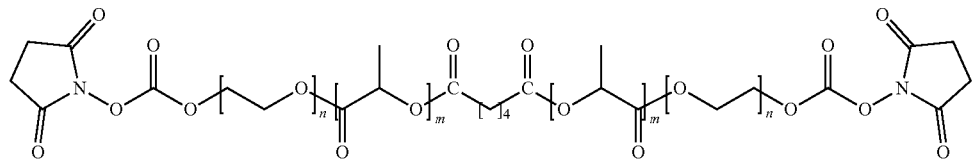

[6] A crosslinking agent containing the triblock copolymer described in [1].

The term "polymer" refers to a molecule that can be obtained from small molecular weight monomers and has a structure composed of repetitions of monomer units. The term "high molecular weight compound" refers to macromolecules obtained by covalently bonding polymers as well as large number of atoms in the manner of proteins and nucleic acids.

The term "average degree of polymerization" as applicable to a polymer refers to the average number of monomer units contained in a single polymer molecule. Namely, polymer molecules of different lengths are present within a polymer composition while dispersed within a certain range.

With respect to the degree of polymerization of a polymer, "number average molecular weight" refers to the average molecular weight per molecule in a polymer composition, while "weight average molecular weight" refers to the molecular weight calculated with the emphasis on weight. In addition, the ratio between number average molecular weight and weight average molecular weight is referred to as the degree of dispersion, and serves as an indicator of the molecular weight distribution of a polymer composition. As the degree of dispersion approaches 1, the average degree of polymerization approaches the actual degree of polymerization in the polymer composition, indicating that a large number of polymer chains of roughly the same length are contained therein.

In the present invention, "biodegradable" means that a substance can be chemically degraded by the action of hydrolysis, enzymatic degradation or microbial degradation and the like.

Additives such as a radical scavenger, peroxide decomposer, antioxidant, ultraviolet absorber, thermal stabilizer, plasticizer, flame retardant or antistatic agent can be added and used as necessary in the injectable gel of the present invention within a range that does not deviate from the gist of the present invention. In addition, a polymer other than the polymer of the present invention can be used by mixing therewith. Such a composition containing the biodegradable injectable gel of the present invention is also an object of the present invention.

The biodegradable injectable gel of the present invention can be used in the form of various types of compositions, such as being able to be used alone by dissolving in a suitable organic solvent, or by mixing with another high molecular weight compound according to the purpose of use. In addition, the medical device of the present invention has the biodegradable injectable gel of the present invention on at least a portion of the surface contacting body tissue or blood. In other words, a composition containing the biodegradable injectable gel of the present invention can be used as a surface treatment agent for the surface of a base material serving as a medical device. In addition, at least a portion of the members of the medical device may be composed with the biodegradable injectable device of the present invention or a composition thereof.

One embodiment of the present invention is the biodegradable injectable gel of the present invention for inhibiting a foreign body reaction to blood or tissue during the time until it degrades when used in contact with body tissue or blood.

The biodegradable injectable gel of the present invention can be preferably used in medical applications. In the case of using the biodegradable injectable gel of the present invention as a composition obtained by mixing with another high molecular weight compound and the like, the composition can be used at a suitable mixing ratio according to the application thereof. In particular, a composition that effectively demonstrates the characteristics of the present invention can be obtained by making the ratio of the biodegradable injectable gel of the present invention to be 90% by weight or more. Other compositions demonstrating various properties can be obtained according to the application by making the ratio of the biodegradable injectable gel of the present invention to be 50% by weight to 70% by weight while maintaining the characteristics of the present invention.

One embodiment of the present invention is a medical device that contains the biodegradable injectable gel of the present invention. Here, a "medical device" includes devices that are temporarily in contact with body tissue in the manner of an artificial organ or other implant and catheter, and is not limited to devices manipulated within the body. In addition, the medical device of the present invention is a device used in medical applications that has the polymer composition of the present invention on at least a portion of the surface thereof. The surface of a medical device as referred to in the present invention refers to, for example, the surface of a material that composes a medical device contacted by blood and the like during use of that medical device, as well as the surface portions of holes within that material.

In the present invention, there are no particular limitations on the material or form of the base material that composes the medical device, and may be in the form of, for example, a porous body, fiber, non-woven fabric, particles, film, sheet, tube, hollow fiber or powder. Examples of the material include natural polymers such as cotton or hemp, synthetic polymers such as nylon, polyester, polyacrylonitrile, polyolefin, halogenated polyolefin, polyurethane, polyamide, polycarbonate, polysulfone, polyether sulfone, poly(meth) acrylate, ethylene-vinyl alcohol copolymer or butadiene-acrylonitrile copolymer, and mixtures thereof. In addition, other examples include metal, ceramics and composite materials thereof, the base material may be composed of a plurality of base materials, and the biodegradable injectable gel according to the present invention is preferably provided on at least a portion of the surface in contact with blood, and more preferably provided over nearly the entire surface in contact with blood.

The biodegradable injectable gel of the present invention can be used as a material that comprises the entirety of a medical device used in contact with body tissue or blood, or can be used as a material that only comprises the surface portion thereof, and at least a portion of the surface in contact with blood, and preferably nearly the entire surface in contact with blood, of an implanted artificial organ or medical device, an extracorporeal circulation type of artificial organ, surgical sutures, catheters (including angiographic catheters, guide wires, PTCA catheters and other circulatory catheters, nasogastric tube catheters, gastrointestinal catheters, feeding tubes and other digestive tract catheters, urinary catheters, ureteral catheters and other urological catheters) and other medical devices are preferably composed with the biodegradable injectable gel according to the present invention. In addition, the biodegradable injectable gel of the present invention can be particularly preferably used in a medical device implanted in the body during treatment by utilizing the biodegradability thereof.

The biodegradable injectable gel of the present invention may also be used as a matrix material of a hemostat, body tissue adhesive material, repair material for tissue regeneration, carrier of a drug gradual-release system, hybrid artificial organ such as an artificial pancreas or artificial liver, artificial blood vessel, embolization material or cell engineering scaffold.

These medical devices may be further imparted with surface lubricity to prevent damage to tissue by facilitating insertion into blood vessels or tissue. An effective method for imparting surface lubricity consists of insolubilizing a water-soluble polymer followed by forming a water-absorbent gel layer on the material surface. According to this method, a material surface can be provided that demonstrates both biocompatibility and surface lubricity.

Although the biodegradable injectable gel of the present invention has superior biocompatibility per se, since it can also be made to further support various physiologically active substances, it can be used in not only blood filters, but also blood storage vessels, blood circuits, indwelling needles, catheters, guide wires, stents, artificial lung machines, dialysis devices, endoscopes and various other medical devices.

More specifically, the biodegradable injectable gel of the present invention may be coated onto at least a portion of the surface of a base material composing a blood filter. In addition, the polymer compound of the present invention may be coated onto at least a portion of the surface of a blood bag and a tube continuous with the aforementioned blood bag that is in contact with blood. In addition, at least a portion of the surface of an extracorporeal circulation blood path in contact with blood, composed of a machine side blood path, consisting of tubes, arterial filters, centrifugal pump, hemoconcentrator and cardioplegia unit, and a surgical field side blood circuit, consisting of a tube, catheter and aspirator, may be coated with the biodegradable injectable gel of the present invention.

In addition, at least a portion of the surface in contact with blood of an indwelling needle assembly, provided with an inner needle having a sharp tip on the end thereof, an inner needle hub installed on the proximal end of the inner needle, a hollow outer needle capable of being inserted with the inner needle, an outer needle hub installed on the proximal end of the outer needle, a protector attached to the inner needle and able to move in the axial direction of the inner needle, and a connecting means for connecting the outer needle hub and the protector, may be coated with the biodegradable injectable gel of the present invention. In addition, at least a portion of the surface of a catheter in contact with blood, composed of a long tube and an adapter connected to the proximal end (nearest end) thereof, may also be coated with the biodegradable injectable gel of the present invention.

In addition, at least at portion of the surface of a guide wire in contact with blood may be coated with the biodegradable injectable gel of the present invention. In addition, at least a portion of the surface in contact with blood of various forms of stents, such as those provided with pores in the side of a hollow tube made of a metal material or polymer material or those molded into a cylindrical shape by weaving wires of a metal material or fibers of a polymer material, may also be coated with the biodegradable injectable gel of the present invention.

In addition, the biodegradable injectable gel of the present invention may be coated onto the outer surface or outer layer of the hollow fiber membranes of a hollow fiber membrane external perfusion type of artificial lung of the type in which, a large number of porous hollow fiber membranes for gas exchange are contained in a housing, blood flows along the outside of the hollow fiber membranes, and oxygen-containing gas flows into the hollow fiber membranes.

In addition, at least a portion of the surface in contact with blood of a dialysis system, having a dialysate circuit containing at least one dialysate container filled with dialysate and at least one drainage container for recovering dialysate, and a pumping means for pumping dialysate from the dialysate container serving as the starting point to the drainage container serving as the finishing point, may be coated with the biodegradable injectable gel of the present invention.

Effects of the Invention

The present invention is a superior scaffold for regenerating cartilage tissue and demonstrates the effect of having superior biodegradability.

BEST MODE FOR CARRYING OUT THE INVENTION

Example 1

Although the following provides a detailed explanation of the present invention through examples thereof, the present invention is not limited to these examples. Furthermore, commercially available products were used as is for the reagents used in the following examples unless specifically indicated otherwise. In the following examples, measurement of the molecular weight distribution of polymers obtained in each of the examples was carried out in the manner indicated below.

Number Average Molecular Weight ([Mn], Units: g/mol)

The number average molecular weight (Mn) and weight average molecular weight (Mw) of polymers were measured (solvent: THF, temperature: 40° C., flow rate: 0.35 mL/min) using polystyrene standards having known peak molecular weights by gel permeation chromatography (GPC) calibrated with the polystyrene standards (Tosoh HLC-8320GPC chromatography system manufactured by Tosoh Corp., column configuration: TSK Guard Column Super MP(HZ)-M, TSKgel Super Multipore HZ-M, four columns connected in series).

Molecular Weight Distribution ([Mw/Mn])

Molecular weight distribution was determined as the ratio (Mw/Mn) obtained using the values for weight average molecular weight (Mw) and number average molecular weight (Mn) determined according the method described above.

NMR Measurement

Polymer structures were analyzed using an NMR measurement system (Bruker Corp., 40 MHz) by $^1$H-NMR measurement and $^{13}$C-NMR measurement. Furthermore, chemical shifts were based on CDCl$_3$ ($^1$H: 7.26 ppm, $^{13}$C: 77.1 ppm).

Synthesis of Bi-Terminally Reactive PEG-PLA-PEG

The overall reaction scheme is indicated below.

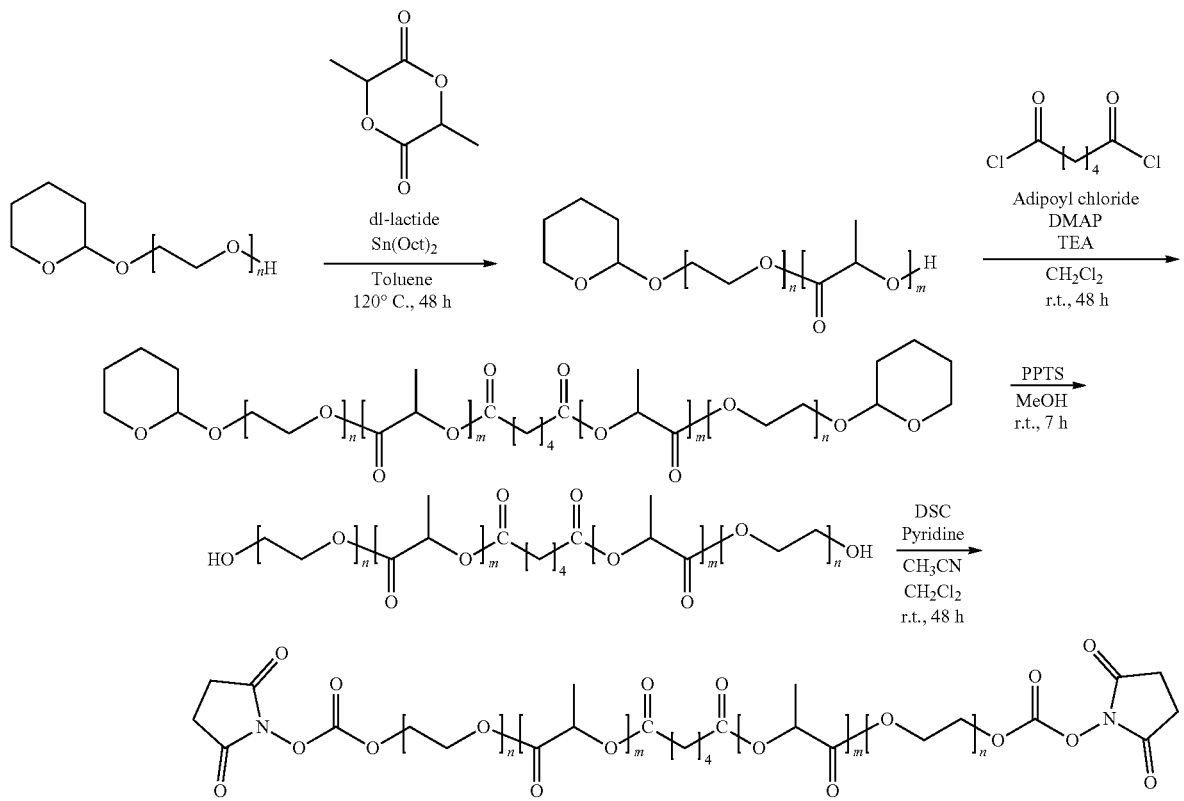

Synthesis of THP-PEG-OH (Mx=2,355)

[Chemical Formula 12]

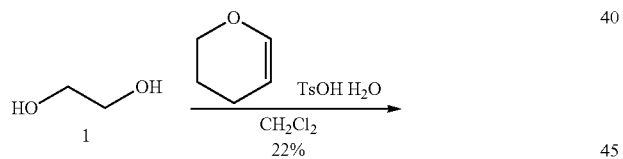

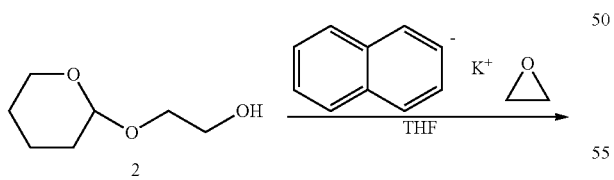

Synthesis of (2)

[Chemical Formula 13]

Figure 20:
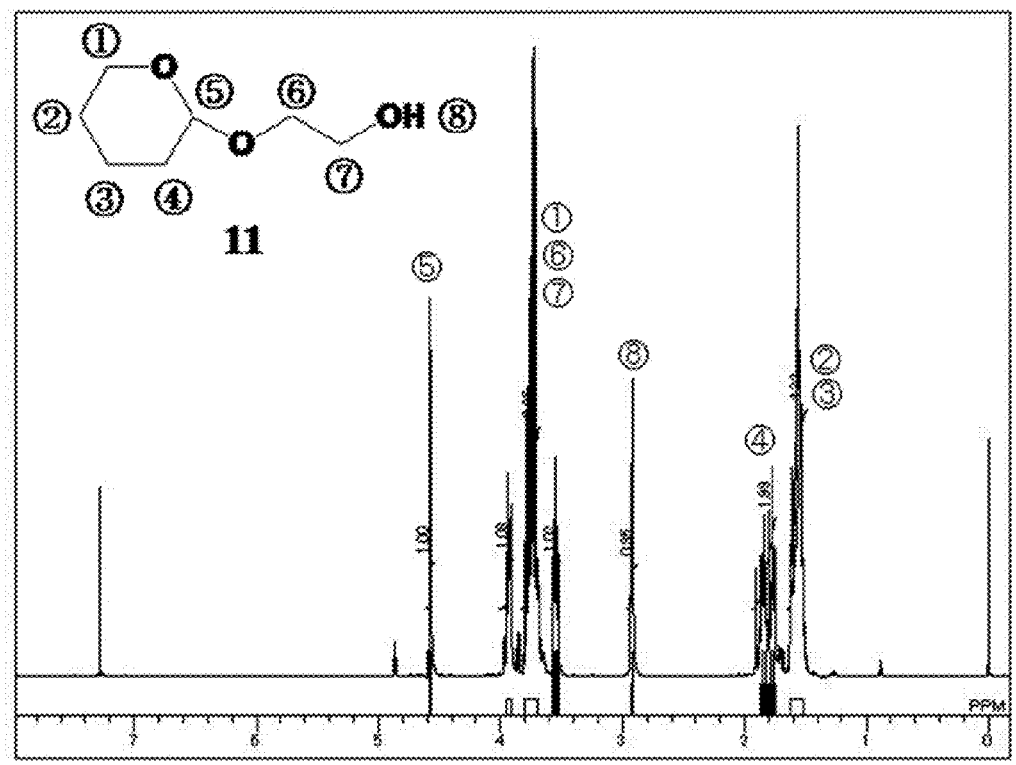
FIG. 20 indicates the $^1$H-NMR spectrum of a product.

15.0 g (223 mmol) of ethylene glycol (1) were dissolved in 200 ml of dichloromethane (anhydrous) in an Ar atmosphere followed by adding 424 mg of TsOH.H$_2$O (2.23 mmol, 1 mol % vs. (1)), slowly dropping in 9.33 g of 3,4-dihydro-2H-pyran (111 mmol, 0.5 eq. vs. (1)) and adding a trace amount of TEA after stirring for 30 minutes at normal temperature. The reaction solution was concentrated and applied to a column (EtOAc/hexane=1/1) to obtain a unilaterally THP-protected form (2) (7.36 g (22%)). Moreover, this was followed by purification by vacuum distillation. $^1$H-NMR (500 MHz, CDCl$_3$): δ 4.58-4.54 (q, 1H, J=2.6 Hz), 3.95-3.51 (m, 6H), 2.92-2.88 (t, 1H, J=5.6 Hz), 1.91-1.75 (m, 6H) (FIG. 20).

Synthesis of (3)

[Chemical Formula 14]

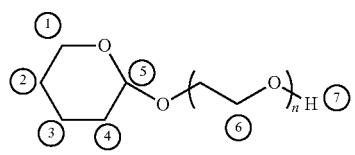

Figure 21:
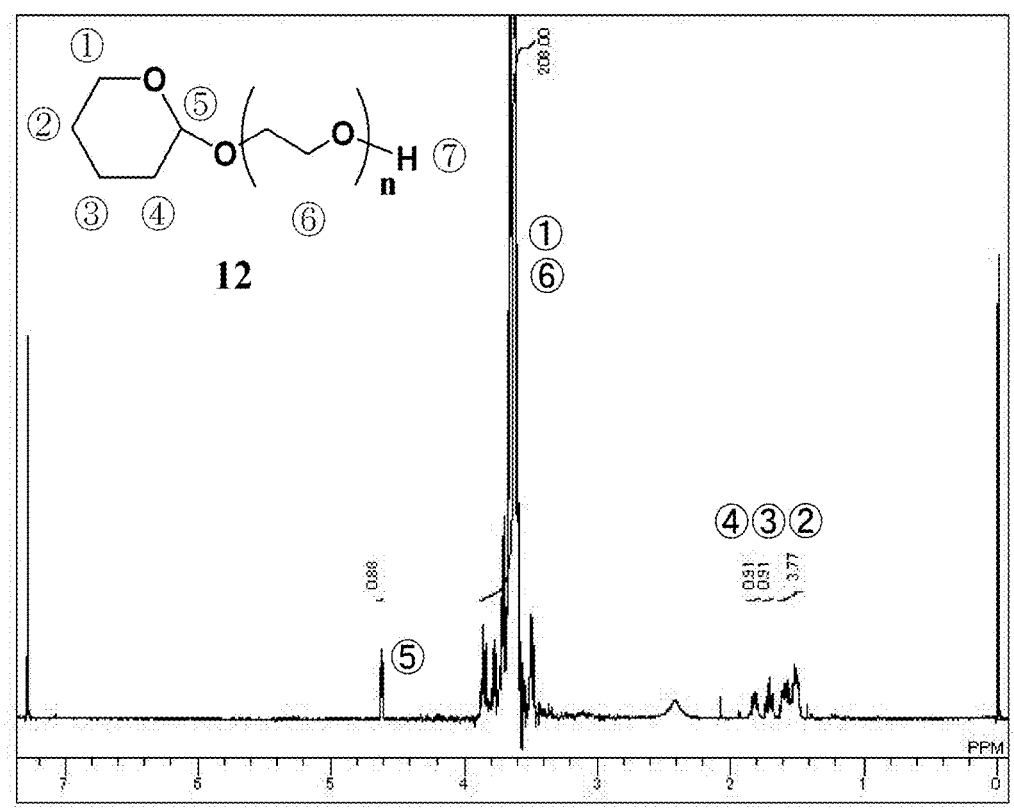
FIG. 21 indicates the $^1$H-NMR spectrum of a product.

146 mg (1 mmol) of (2) were placed in an atmosphere replaced with Ar {vacuum: 15 minutes+Ar}×3} followed by adding 15 ml of THF (anhydrous) in the presence of flowing Ar and dropping 1 mmol of potassium naphthalene into the THF to carry out metalation. Following metalation, 2.5 ml (50 mmol) of ethylene oxide were dropped in in the presence of flowing Ar followed by stirring for 2 days at normal temperature. The reaction solution was purified by re-precipitation with 400 ml of diethyl ether to obtain THP-PEG-OH (3) by freeze-drying (2.2 g (recovery rate: 100%)). GPC number average molecular weight (Mn)=2355, Mw/Mn=1.07, $^1$H-NMR (500 MHz, CDCl$_3$): δ 4.63-4.6 (t, 1H), 3.90-3.37 (m, 208H), 1.89-1.47 (m, 8H) (FIG. 21).

Synthesis of THP-PEG-PLA-OH

[Chemical Formula 15]

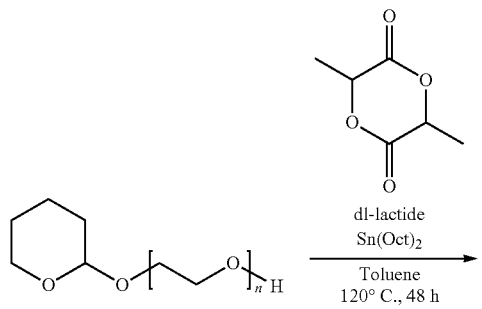

2000 mg (0.8493 mmol) of THP-PEG-OH (Mn=2,356, Mw/Mn=1.094), 979.2 mg of dl-lactide (recrystallized) (6.794 mmol, 8 eq. vs. THP-PEG-OH) and 34.40 mg of Sn(Oct)$_2$ (0.0849 mmol, 0.1 eq. vs. THP-PEG-OH) were dissolved in 97.92 mL of toluene (dl-lactide: 10 mg/mL) in an N$_2$ atmosphere followed by stirring for 48 hours at 120° C. Following the reaction, the reaction solution was concentrated and re-precipitated with diethyl ether. After freeze-drying with benzene, the structure of the compound was analyzed by $^1$H-NMR (yield: 2531 mg, yield rate: 85.0%, FIG. 1).

Figure 1:
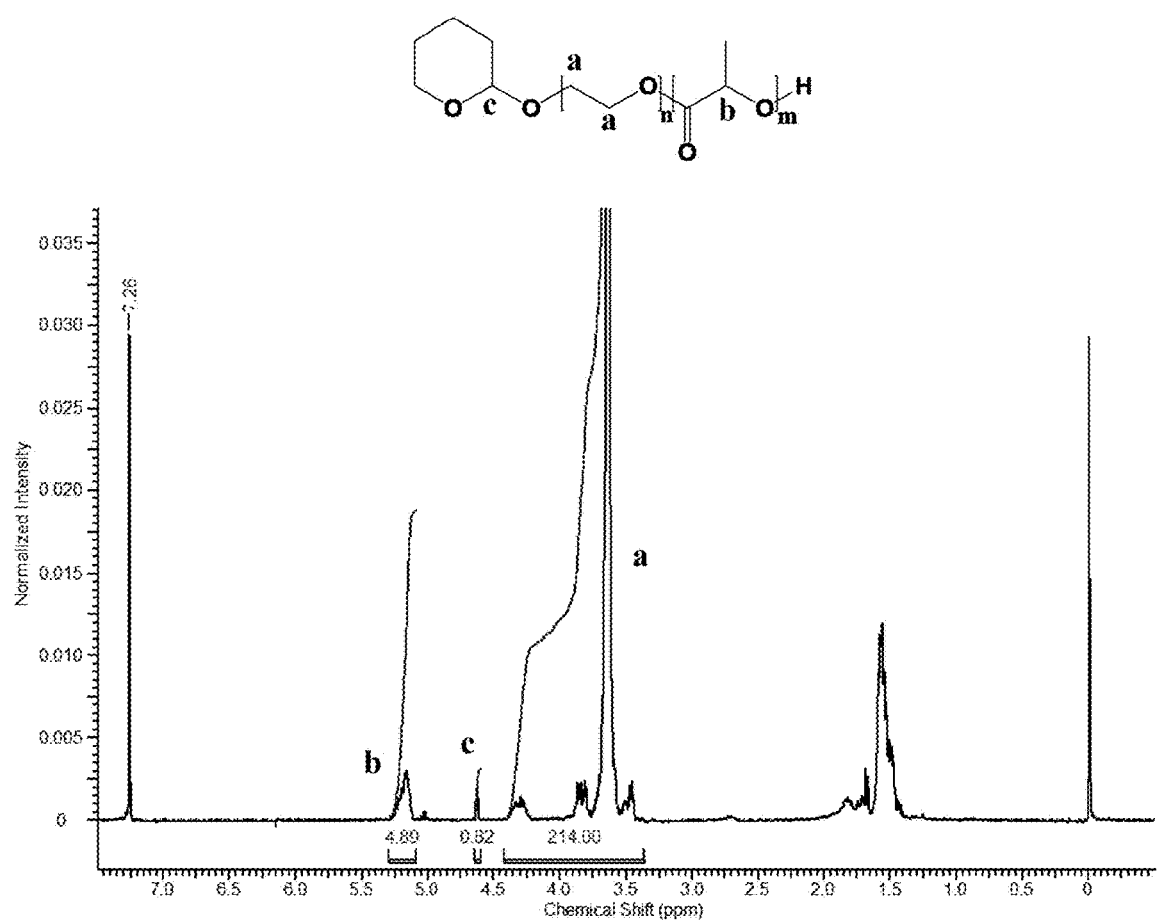
FIG. 1 indicates the $^1$H-NMR spectrum of a product.

Protons were assigned according to FIG. 1. A value of 214.00 was used as the basis for calculated values based on the EO chain-derived peak a of PEG. The number of PLA chains was determined to be 5 based on the value of the PLA-derived peak b.

Synthesis of THP-PEG-PLA-PEG-THP

[Chemical Formula 16]

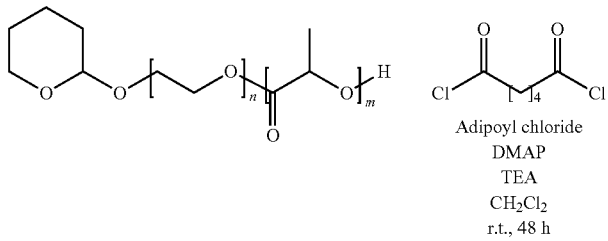

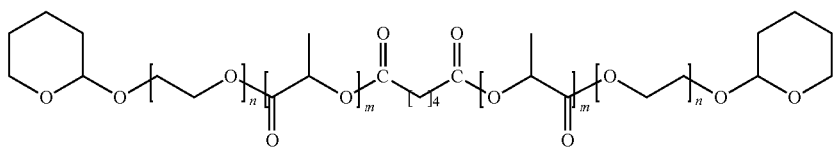

2000 mg (0.7366 mmol) of THP-PEG-PLA-OH and 539.9 mg of DMAP (4.419 mmol, 3.0 eq. vs. THP-PEG-PLA-OH) were dissolved in 30 mL of $CH_2Cl_2$ in an $N_2$ atmosphere followed by the addition of 411 μL of TEA (2.946 mmol, 2 eq. vs. THP-PEG-PLA-OH) and stirring for 10 minutes while cooling with ice (0° C.). After mixing in 67.41 mg of adipoyl chloride (0.3683 mmol, 0.5 eq. vs. THP-PEG-PLA-OH) dissolved in 20 mL of $CH_2Cl_2$, the mixture was stirred for 48 hours at room temperature. Following the reaction, the product was washed with 1 N HCl and Milli-Q water and this procedure was repeated twice. Moreover, after adding $MgSO_4$ and concentrating, the product was freeze-dried with benzene. The structure of the resulting compound was analyzed by $^1$H-NMR and GPC (yield: 1619 mg, yield rate: 79.3%, FIG. 2).

Figure 2:
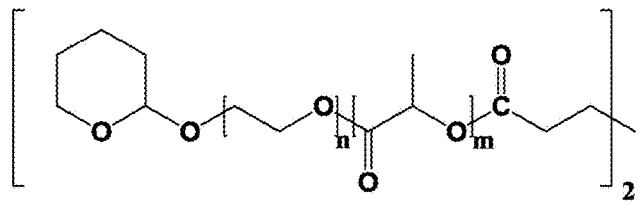
FIG. 2 indicates the $^1$H-NMR spectrum of a product.
Figure 2:
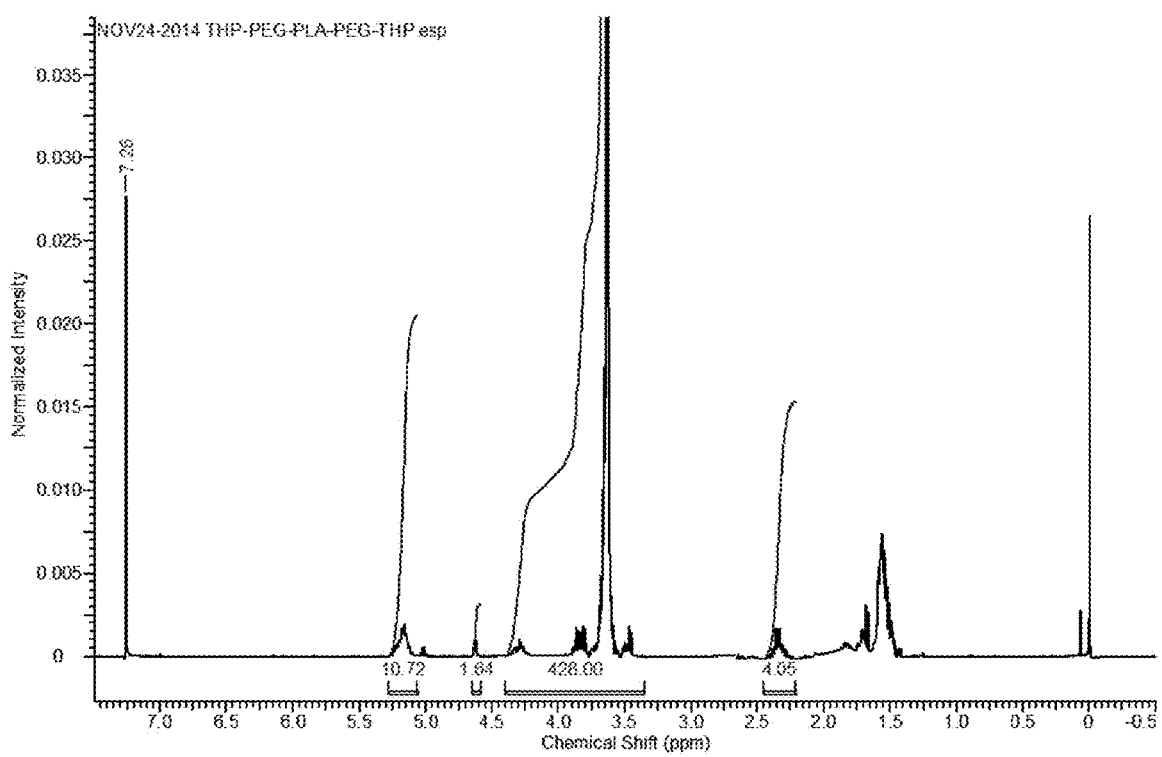
Figure 3:
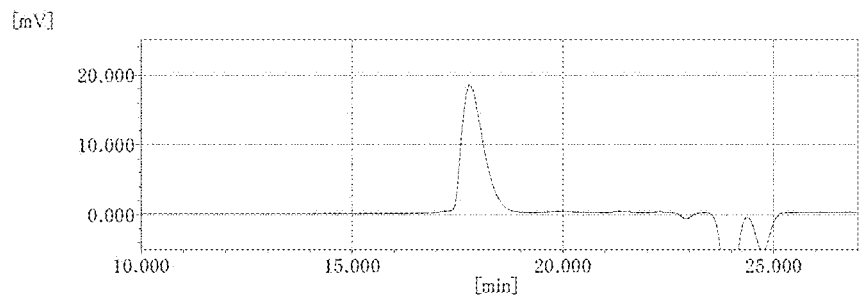
FIG. 3 indicates the results of GPC measurement of a product.
Figure 3:
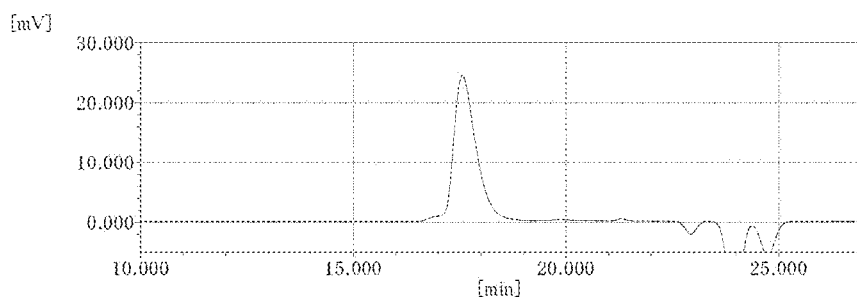
Figure 3:
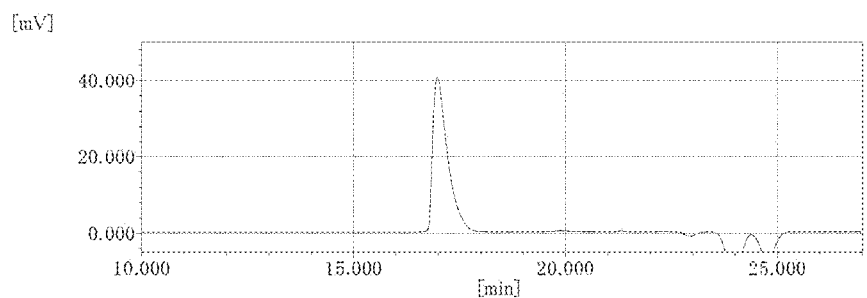

Protons were assigned according to FIG. 2. A value of 428.00 was used as the basis for calculated values based on the EO chain-derived peak a of PEG assuming that THP-PEG-PLA-OH was completely bound to both ends of the adipoyl chloride. The number of PLA chains was determined to be 10 based on the value of the PLA-derived peak b. In addition, GPC measurement results are shown in FIG. 3.

As a result of GPC measurement, unimodal elution peaks shifted to the high molecular weight side in the order of THP-PEG-OH, THP-PEG-PLA-OH and THP-PEG-PLA-PEG-THP. On the basis of these results, THP-PEG-PLA-PEG-THP was confirmed to have been synthesized.

Synthesis of OH-PEG-PLA-PEG-OH

[Chemical Formula 17]

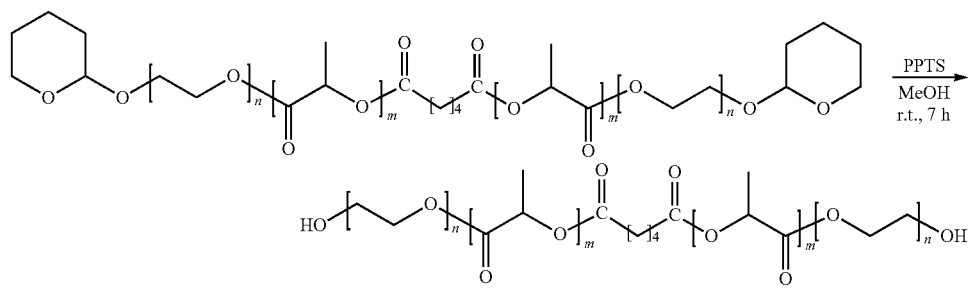

1500 mg (0.2707 mmol) of THP-PEG-PLA-PEG-THP and 68.03 mg of pyridinium para-toluenesulfonate (PPTS, 0.2707 mmol, 1.0 eq. vs. THP-PEG-PLA-PEG-THP) were dissolved in 20 mL of MeOH in an $N_2$ atmosphere followed by stirring for 7 hours at room temperature. Following the reaction, the reaction solution was concentrated and re-precipitated with diethyl ether. After freeze-drying with benzene, the structure of the resulting compound was analyzed by $^1$H-NMR (yield: 1385 mg, yield rate: 95.2%, FIG. 4).

Figure 4:
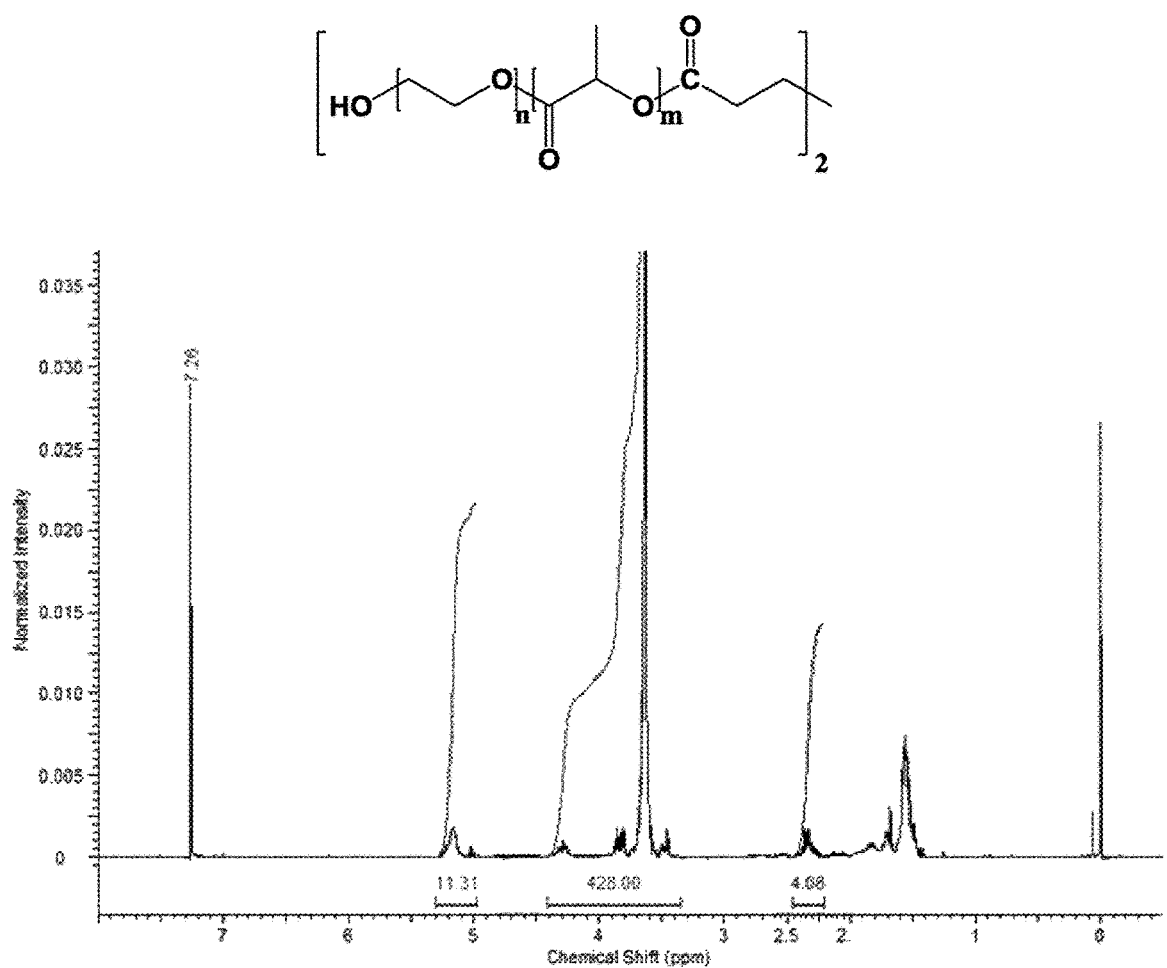
FIG. 4 indicates the $^1$H-NMR spectrum of a product.

Protons were assigned according to FIG. 4. A value of 428.00 was used as the basis for calculated values based on the EO chain-derived peak a of PEG. The THP protecting groups were confirmed to have been removed since the peak derived from THP was no longer observed.

Synthesis of NHS-PEG-PLA-PEG-NHS

[Chemical Formula 18]

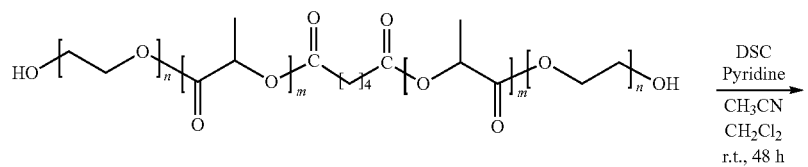

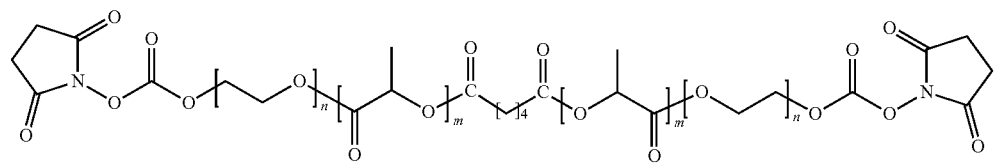

1200 mg (0.2232 mmol) of OH-PEG-PLA-PEG-OH were dissolved in 50 mL of $CH_2Cl_2$ in an $N_2$ atmosphere. Separate from this, 285.9 mg (1.116 mmol) of di(N-succinimidyl) carbonate (DSC) were dissolved in 20 mL of $CH_3CN$ at 60° C. over the course of 30 minutes. After mixing the 20 mL of the DSC solution with the 50 mL of the PEG solution, 200 μL of pyridine were added followed by stirring for 48 hours at room temperature. Following the reaction, the reaction solution was filtered and concentrated followed by re-precipitating with diethyl ether. After freeze-drying with benzene, the structure of the resulting compound was analyzed by $^1$H-NMR (yield: 1142 mg, yield rate: 90.1%, FIG. 5).

Figure 5:
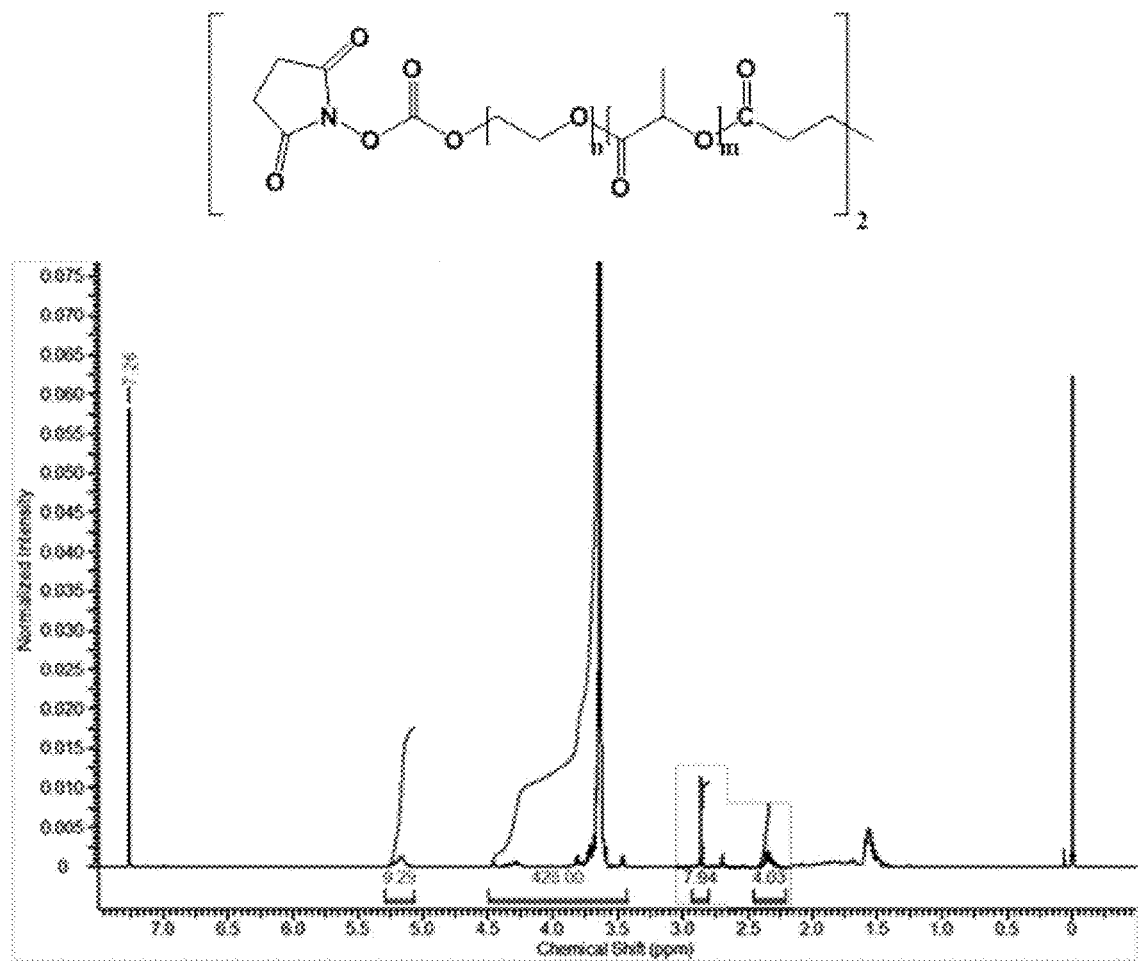
FIG. 5 indicates the $^1$H-NMR spectrum of a product.

Protons were assigned according to FIG. 5. A value of 428.00 was used as the basis for calculated values based on the EO chain-derived peak a of PEG. The rate of conversion to NHS was determined to be 99.3% based on the NHS-derived peak.

Preparation of Chitosan/PEG-PLA-PEG/RADA Gel and Evaluation of Properties

Preparation of 300 μL of Chitosan/PEG (2.0/1.0 wt %) Gel

150 μL of PBS were added to 100 μL of 6.0% by weight chitosan prepared using PBS (150 mM, pH 7.4). 50 μL of 6.0% by weight bi-terminated NHS-PEG prepared using PBS (150 mM, pH 7.4) were then added thereto.

Preparation of 300 μL of Chitosan/PEG/RADA16 (2.0/1.0/0.25 wt %)

75 μL of PBS (300 mM, pH 7.4) were added to 100 μL of 6.0% by weight chitosan prepared using PBS (150 mM, pH 7.4). 50 μL of 6.0% by weight bi-terminated NHS-PEG prepared using PBS (150 mM, pH 7.4) were then added thereto followed by promptly adding 75 μL of a 1.0% by weight aqueous solution of RADA16.

[Preparation of Gelation Phase Diagrams]

Experimental Procedure

Figure 6:
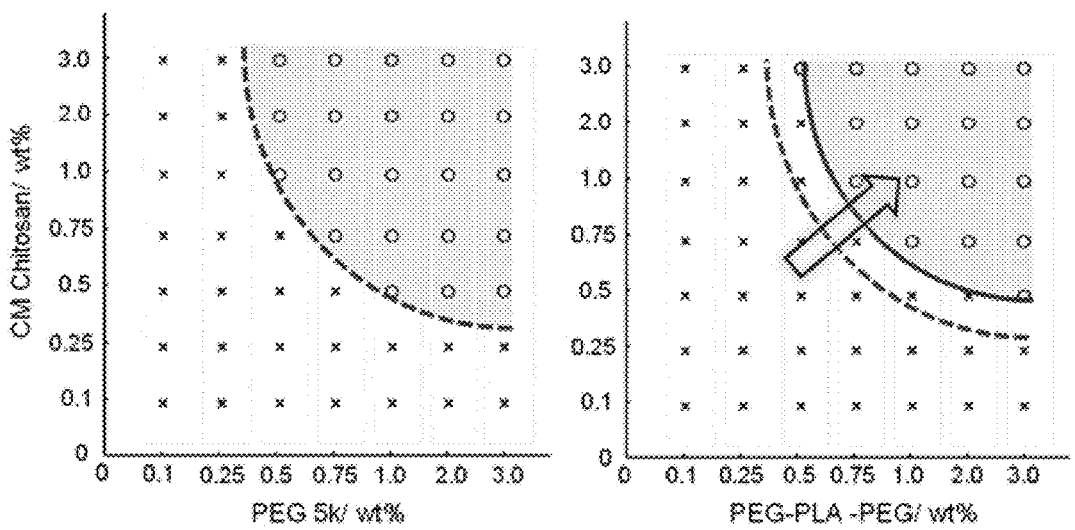
FIG. 6 shows gelation phase diagrams in the case of using PEG 5k and PEG-PLA-PEG (left: chitosan/PEG 5k, right: chitosan/PEG-PLA-PEG).

Gelation of the solutions was evaluated using a tilting test after allowing to stand undisturbed for 20 minutes. Gelation phase diagrams were prepared after observing the gelation behavior of each solution. The target concentrations of chitosan/PEG-PLA-PEG gels were prepared by suitably modifying the mixing ratio of chitosan, PEG-PLA-PEG and PBS. The final concentration of PBS in all gels was adjusted to 150 mM by suitably using PBS having different ion concentrations. The gelation phase diagrams are shown in FIG. 6.

Chitosan/PEG-PLA-PEG was confirmed to gel over a high concentration range in comparison with that of PEG 5k. This is thought to be caused by a decrease in solvation due to containing PLA and resulted in a reduction in reactivity. In addition, PEG-PLA-PEG is known to only form a physically crosslinked gel by temperature phase transition (Sol-Gel transition) at high concentrations in the manner of 30% by weight at room temperature (T. Mukose, et al., Macromol. Biosci., 2014, 4, 361-367). Since the gelation of this system occurs over an extremely low concentration range, gelation was suggested to have occurred based on the formation of chemical crosslinks between molecular chains.

Measurement of Frequency Dependency

Figure 7:
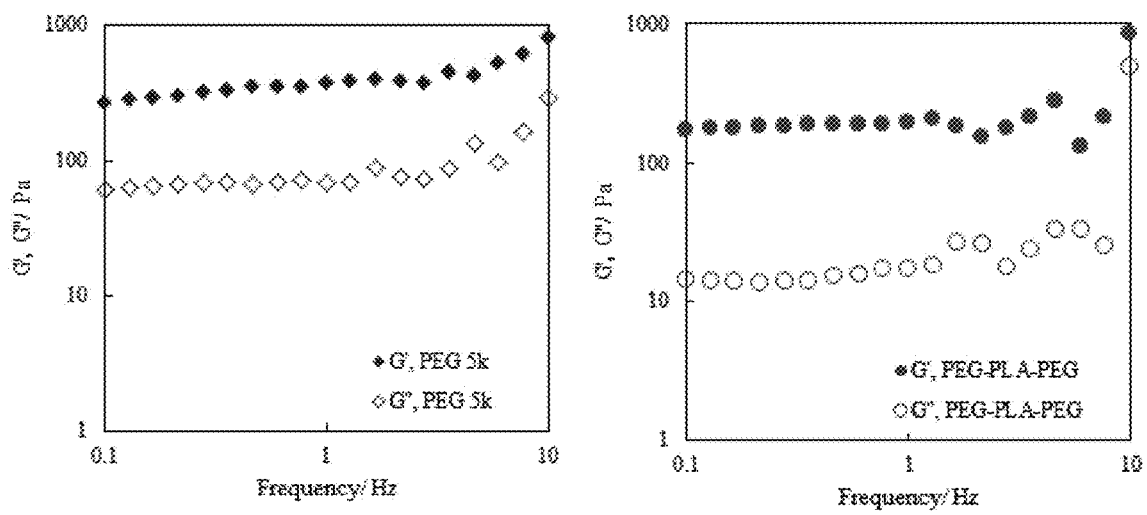
FIG. 7 indicates the results of measuring frequency dependency in the case of using PEG 5k and PEG-PLA-PEG (left: chitosan/PEG 5k, right: chitosan/PEG-PLA-PEG).

Gel having a volume of 300 μL was molded into the shape of a disk having a diameter of 15 mm. After allowing to swell for 24 hours (4° C.) in PBS (150 mM, pH 7.4), the swollen gel was placed on a mounting stand. Parallel plates were placed in close proximity so as to apply a load of 0.5 N. During frequency measurement, shear strain stress was set to 1% (=γ) and oscillation frequency was measured over a range of 0.1 Hz to 100 Hz (FIG. 7). Storage modulus (G') was higher than loss modulus (G") in both cases and typical gel properties were confirmed.

Observation of Gelation Behavior

Figure 8:
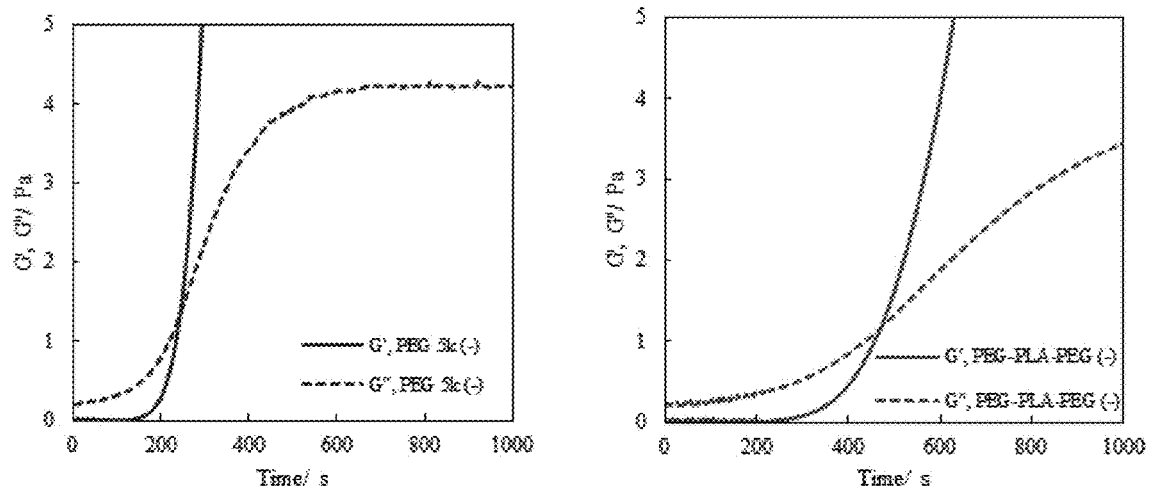
FIG. 8 indicates gelation behavior in the case of using PEG 5k and PEG-PLA-PEG (left: chitosan/PEG 5k, right: chitosan/PEG-PLA-PEG).

Gelation behavior was evaluated by preparing a gel precursor solution having a volume of 210 μL on a rheometer stand using a method similar to a typical gel preparation method, followed immediately by beginning measurement of viscoelasticity. The measurement frequency was 1 Hz and load was measured at 1 Pa. Furthermore, gelation of RADA was observed by adding 52.5 μL of a 1.0% by weight aqueous solution of RADA16 to 157.5 μL of PBS (200 mM, pH 4.7) (FIG. 8).

In both cases, G' increased rapidly after the passage of a prescribed amount of time and a well-defined gel point was observed (G'>G"). In addition, a decrease in the gelation rate was observed in the case of using PEG-PLA-PEG. This is due to a decrease in solvation due to containing PLA and resulted in a reduction in the reaction rate.

Figure 9:
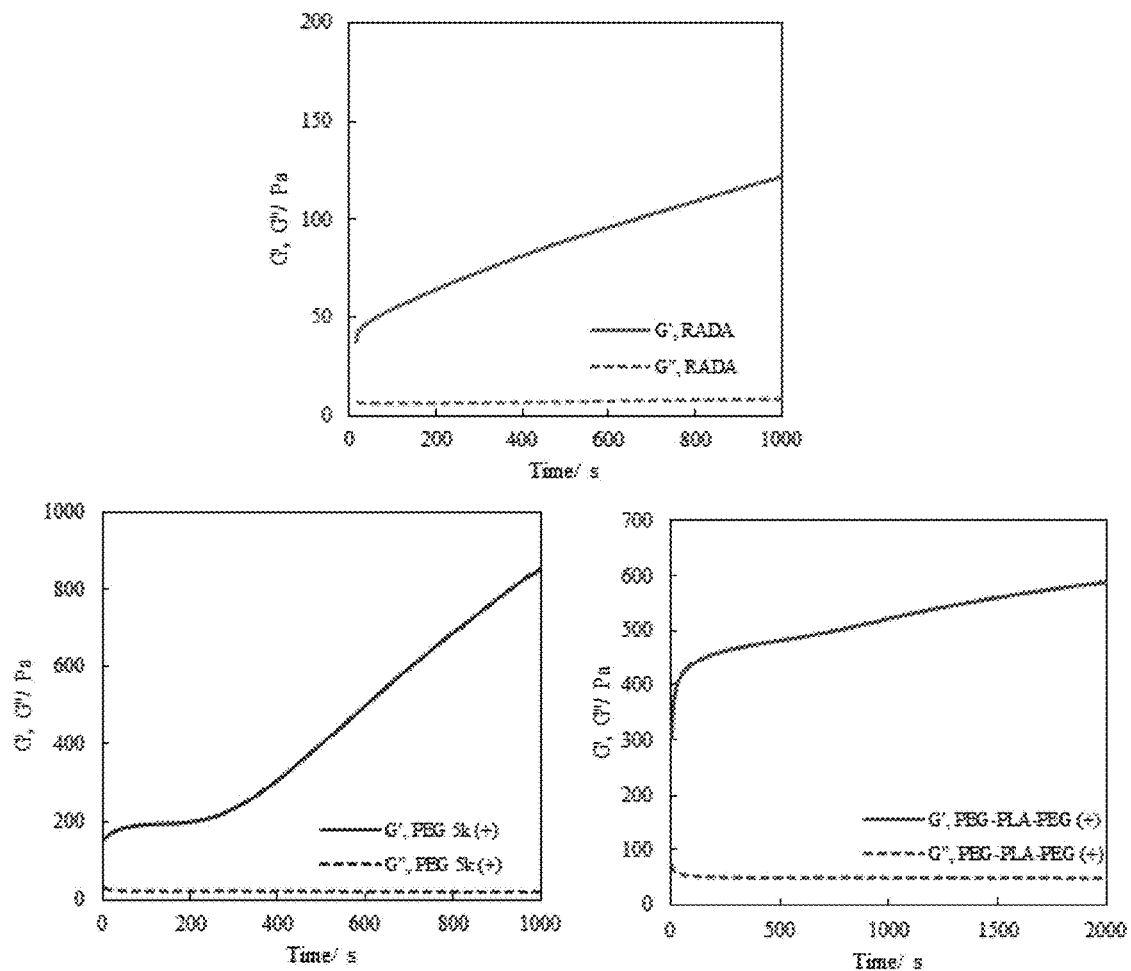
FIG. 9 indicates gelation behavior of RADA mixed systems.

Next, the results of observing gelation behavior in the RADA mixed systems are shown (FIG. 9). In the case of the RADA16 peptide gel, G' was higher than G" at the start of measurement, suggesting that gelation occurred immediately as a result of mixing with PBS. In addition, the value of G' increased considerably in comparison with the case of each gel alone as a result of mixing in RADA. Moreover, G' changed in multiple stages with the passage of time, and the inflection points thereof exhibited a high correlation with the gelation time of chitosan/PEG-PLA-PEG. On the basis of these results, chitosan/PEG/RADA16 and chitosan/PEG-PLA-PEG/RADA16 were suggested to have formed a network of RADA16 followed by the formation of an inter-penetrating polymer network (IPN) in which chitosan/PEG and chitosan/PEG-PLA-PEG formed crosslinks there between.

Measurement of Mechanical Strength

Gel having a volume of 300 μL was molded into the shape of a disk having a diameter of 15 mm. After allowing to swell for 24 hours (4° C.) in PBS (150 mM, pH 7.4), the swollen gel was placed on a mounting stand.

Figure 10:
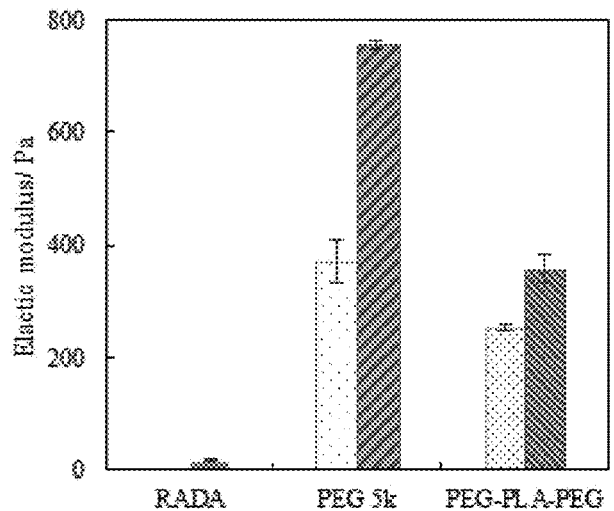
FIG. 10 indicates Young's modulus in the case of using PEG 5k and PEG-PLA-PEG (dots) and Young's modulus in RADA mixed systems (diagonal lines).

After setting the frequency to a constant frequency of 1 Hz, mechanical strength was measured by applying a pressure ranging from 1 Pa to 3000 Pa to each gel sample. The point at which loss modulus G" exceeded storage modulus G' was defined as the breaking point of the gel and a stress-strain curve was prepared on the basis thereof. Young's modulus was calculated by approximating the initial slope of the resulting stress-strain curve to be a straight line (FIG. 10).

Mechanical strength of the chitosan/PEG-PLA-PEG gel was lower than that of the chitosan/PEG 5k gel. This is thought to be due to a decrease in reactivity caused by introduction of PLA, which in turn caused a decrease in mechanical strength.

In addition, in both cases, mechanical strength improved as a result of containing peptide. This is due to compounding of the gel network, suggesting the formation of an IPN structure.

Measurement of Degree of Swelling

Figure 11:
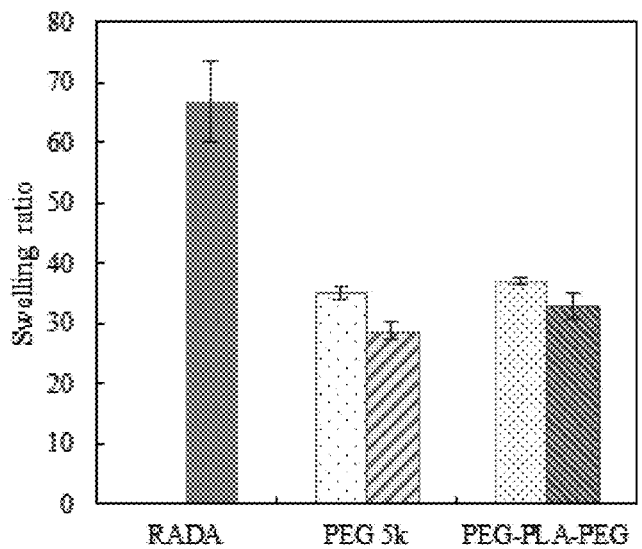
FIG. 11 indicates degree of swelling in the case of using PEG 5k and PEG-PLA-PEG (dots) and degree of swelling in RADA mixed systems (diagonal lines).
Figure 12:
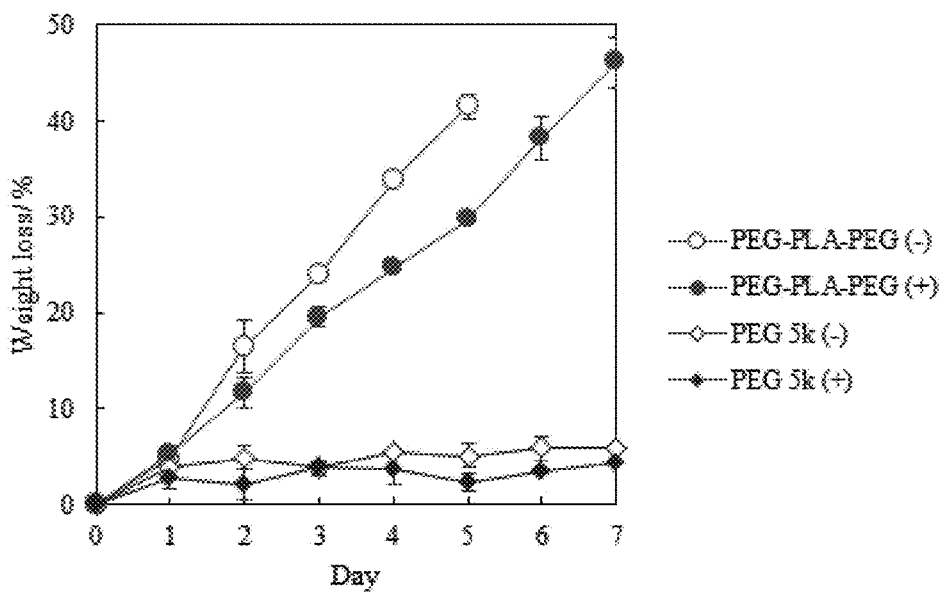
FIG. 12 indicates degradation behavior under acidic conditions in the case of using PEG 5k and PEG-PLA-PEG in the presence or absence of mixing with RADA.

After preparing gel having a volume of 300 μL and allowing to swell for 48 hours (4° C.) in PBS (150 mM, pH 7.4), the weight of the gel after swelling was measured. After freeze-drying each sample for 24 hours, the weight of the gel was measured again. The degree of swelling Q0 was calculated using the equation indicated below (FIG. 11).

$Q0=(W_s-W_d)/W_d$ $W_s$:Weight of swollen gel, $W_d$:Weight of Dry Gel

The degree of swelling of the chitosan/PEG-PLA-PEG gel was higher than that of the chitosan/PEG 5k gel. This is thought to be due to a decrease in reactivity caused by introduction of PLA, which in turn caused the degree of swelling to increase. In addition, in both cases, the degree of swelling decreased significantly as a result of containing peptide. This suggests an increase in network density based on the formation of an IPN structure.

Evaluation of Degradation Behavior

A degradation test conducted regarding the following:

acid-accelerated degradation test (acetic acid, room temperature conditions, and experimental procedure.

Gels having a volume of 300 μL were respectively prepared and allowed to swell for 48 hours (4° C.) in 1 mL of PBS (150 mM, pH 7.4). After the gels had swollen, the PBS was removed followed by the addition of 1 mL of $CH_3COOH$ and allowing to stand undisturbed under room temperature conditions. After a prescribed amount of time had elapsed, the samples were washed three times using PBS followed by measuring the swollen weight of the gels. After freeze-drying each sample for 24 hours, the dry weight of the gels was measured. Degree of swelling Q and weight loss were calculated using the equations indicated below. The solutions were replaced once a day (FIG. 2).

$$Q=(W_s-W_d)/W_d$$

$W_s$:Weight of swollen gel, $W_d$:Weight of dry gel $$\text{Weight loss (\%)}=(W_{d0}-W_d)/W_{d0}\times 100$$

$W_{d0}$=initial dry weight(day 0)

The gel using PEG 5k did not exhibit degradation behavior. On the other hand, in the gel using PEG-PLA-PEG, remarkable degradation behavior was confirmed regardless of the presence or absence of RADA. Degradation behavior based on hydrolysis of PLA was confirmed to be demonstrated in the case of using PEG-PLA-PEG.

Degradation Test under Physiological Conditions (PBS (150 mM, pH 7.4), 37° C.)

Figure 13:
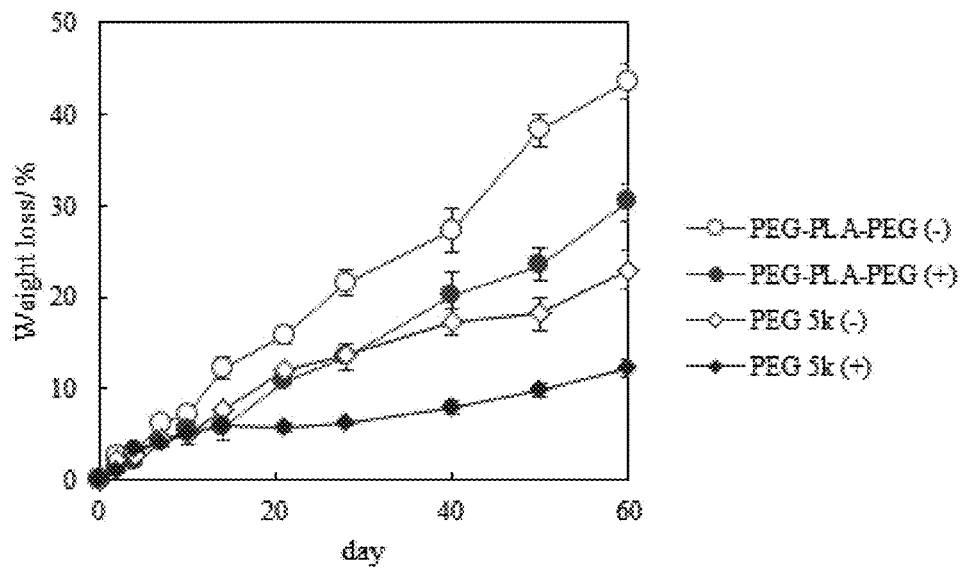
FIG. 13 indicates degradation behavior under physiological conditions in the case of using PEG 5k and PEG-PLA-PEG in the presence or absence of mixing with RADA.
Figure 14:
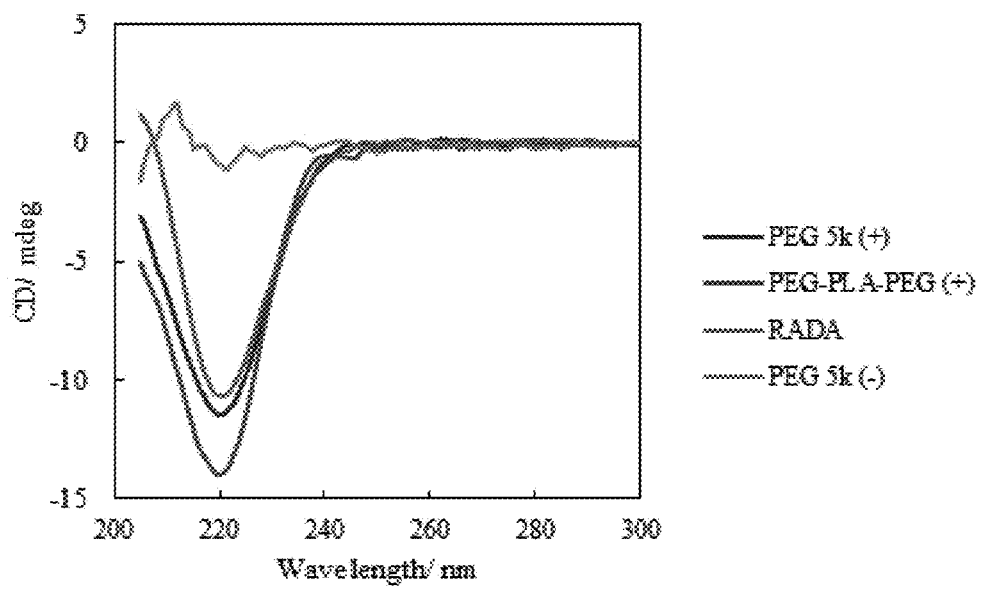
FIG. 14 indicates the results of measuring CD spectra in various hydrogels.
Figure 15:
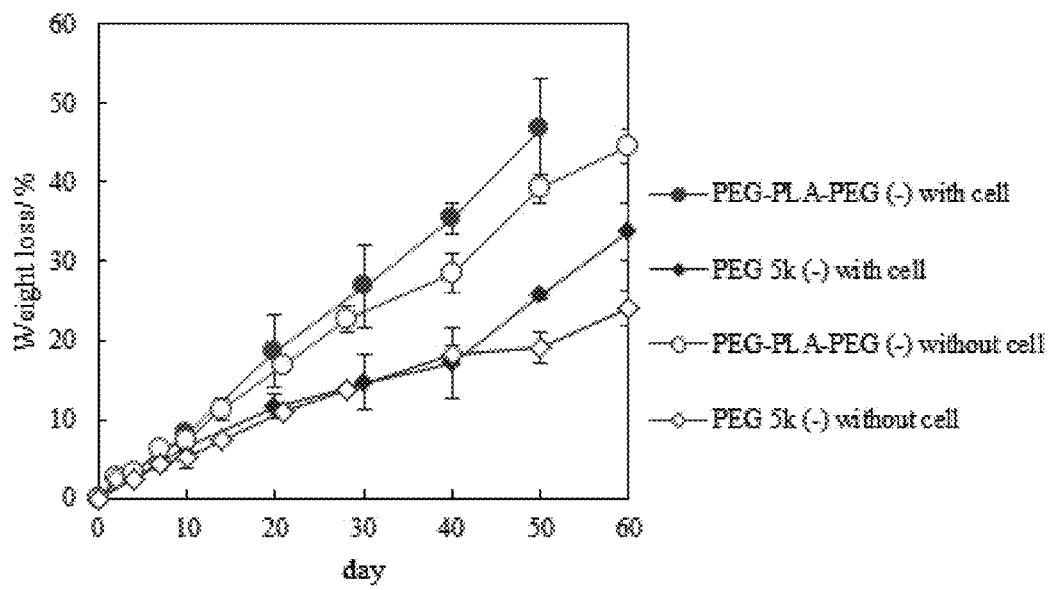
FIG. 15 indicates degradation behavior of chitosan/PEG 5k gel and chitosan/PEG-PLA-PEG gel in the presence of cells.

Gels having a volume of 300 μL were respectively prepared and allowed to swell for 48 hours (4° C.) in 1 mL of PBS (150 mM, pH 7.4). After allowing the gels to swell, the PBS was removed followed by the addition of 1 mL of fresh PBS and allowing to stand under conditions of 37° C. After a prescribed amount of time had elapsed, the samples were washed three times using PBS followed by measurement of the swollen weight of the gels. After freeze-drying each sample for 24 hours, the dry weight of the gels was measured. Degree of swelling Q and weight loss were calculated using the equations indicated below. The solutions were replaced every 3 days (FIG. 13).

$$Q=(W_s-W_d)/W_d$$

$W_s$:Weight of swollen gel, $W_d$:Weight of dry gel $$\text{Weight loss (\%)}=(W_{d0}-W_d)/W_{d0}\times 100$$

$W_{d0}$=initial dry weight(day 0)

Increases in weight loss accompanying outflow of non-crosslinked chains was confirmed in the initial stages for PEG-PLA-PEG and RADA. In the case of using PEG-PLA-PEG, gradual degradation behavior was confirmed regardless of the presence or absence of RADA. Degradation rate accelerated in comparison with the case of using PEG 5k, and degradation behavior accompanying hydrolysis of PLA was similarly confirmed even under physiological conditions.

Measurement of Circular Dichroism (DC) Spectrum

Samples having a volume of 90 μL were respectively prepared and coated onto a quartz cell having an optical path length of 0.1 mm. Measurement conditions were as indicated below.

Measurement wavelength: 300 nm to 205 nm
Data interval: 0.5 nm
Scanning speed: 200 nm/min
No. of scans: 3
Response time: 2.0 s
Bandwidth: 1.0 nm
Measurement temperature: 20° C.

RADA is known to exhibit a negative Cotton effect based on a β sheet structure in the vicinity of 220 nm of the CD spectrum. Since negative Cotton effects were similarly obtained in the gels containing peptide, the fiber structure of the peptide was determined to be stably retained within the gel.

Cell Culturing of Chitosan/PEG-PLA-PEG/RADA Gel (1) A 4% by weight chitosan solution (150 mM PBS) was prepared using chitosan (carboxymethyl chitosan, Koyo Chemical Co., Ltd.) preliminarily subjected to UV sterilization treatment for 20 minutes.

(2) Subconfluent bovine chondrocytes (P1) preliminarily cultured in an incubator (37° C., 5% $CO_2$) were detached from the plate by treating with trypsin followed by centrifuging (1,500 rpm, 5 minutes) and removing the supernatant.

(3) 10 mL of DMEM medium were added followed by measuring the number of cells.

(4) After centrifuging (1,500 rpm, 5 minutes) and removing the supernatant, a cell suspension was prepared using a 4% by weight chitosan solution.

(5) 25 μL of the cell suspension were added to a 1.5 mL sampling tube.

(6) A 4% by weight PEG solution (in 300 mM PBS) was separately prepared using NHS-PEG-PLA-PEG-NHS subjected to UV treatment for 20 minutes.

(7) 12.5 μL of the 4% by weight PEG solution of (6) were added to the cell suspension of (5) followed by the addition and mixing of 12.5 μL of a 1.0% by weight RADA16 solution immediately after pipetting. Furthermore, in the case of using chitosan/PEG-PLA-PEG (2.0% by weight/1.0% by weight), an equal volume of 150 mM PBS was added instead of the RADA16 solution.

(8) After allowing to gel for 10 minutes, 500 μL of DMEM (10% FBS, 2% Pen-Strep) were added to the upper portion of the gel followed by culturing in an incubator (37° C., 5% $CO_2$). Samples of the medium were recovered and 500 μL of fresh DMEM were added every two to three days. The recovered medium samples were stored at −80° C.

Gel Compositions:
1. Chitosan/PEG 5k=2.0% by weight/1.0% by weight
2. Chitosan/PEG-PLA-PEG=2.0% by weight/1.0% by weight
3. Chitosan/PEG 5k/RADA16=2.0% by weight/1.0% by weight/0.25% by weight 4. Chitosan/PEG-PLA-PEG/RADA16=2.0% by weight/1.0% by weight/0.25% by weight Culturing Conditions:
Cell count: $5.0\times 10^5$ cells
Cell density: $1.0\times 10^7$ cells/ml
Gel volume: 50 μL
Media volume: 500 μL Evaluation of Effect of Chitosan/PEG-PLA-PEG/RADA Gel on Chondrocyte Function Evaluation of Degradation Behavior (in Presence of Cells)

Chitosan/PEG 5k gel and chitosan/PEG-PLA-PEG gel having a volume of 300 μL were respectively prepared using the same method as described above followed by the addition of 1 mL of DMEM and allowing to stand undisturbed under conditions of 37° C. and 5% $CO_2$. After a prescribed amount of time had elapsed, the samples were washed three times using PBS and each sample was freeze-dried for 24 hours followed by measuring the dry weight of the gel. Weight loss was calculated using the equation indicated below. The medium was replaced every two to three days.

Weight loss (%)=$(W_{d0}-W_d)/W_{d0} \times 100$ $W_{d0}$=initial dry weight(day 0)

Culturing Conditions:
Cell count: $3.0 \times 10^6$ cells
Cell density: $1.0 \times 10^7$ cells/ml
Gel volume: 300 μL
Media volume: 1000 μL In the presence of cells, the chitosan/PEG 5k gel did not exhibit prominent degradation behavior through day 40, while the chitosan/PEG-PLA-PEG gel exhibited gradual degradation behavior over time. Thus, the chitosan/PEG-PLA-PEG gel was suggested to exhibit similar degradation behavior attributable to PLA in the presence of cells as well. In addition, in the chitosan/PEG 5k gel starting on day 40, crosslinked chains were cleaved as the cells spread, and this gel is thought to have exhibited prominent degradation behavior as a result thereof.

MTT Assay (1) 450 μL of DMEM and 50 μL of 5 mg/mL MTT reagent were added when the sample medium was replaced.

(2) The cells were incubated for 24 hours (37° C., 5% $CO_2$).

(3) The supernatant was removed and the cells were disrupted followed by adding 500 μL of MTT extraction reagent (2-propanol:1 M HCl=24 vol %:1 vol %) and shaking for 24 hours at 37° C.

Figure 16:
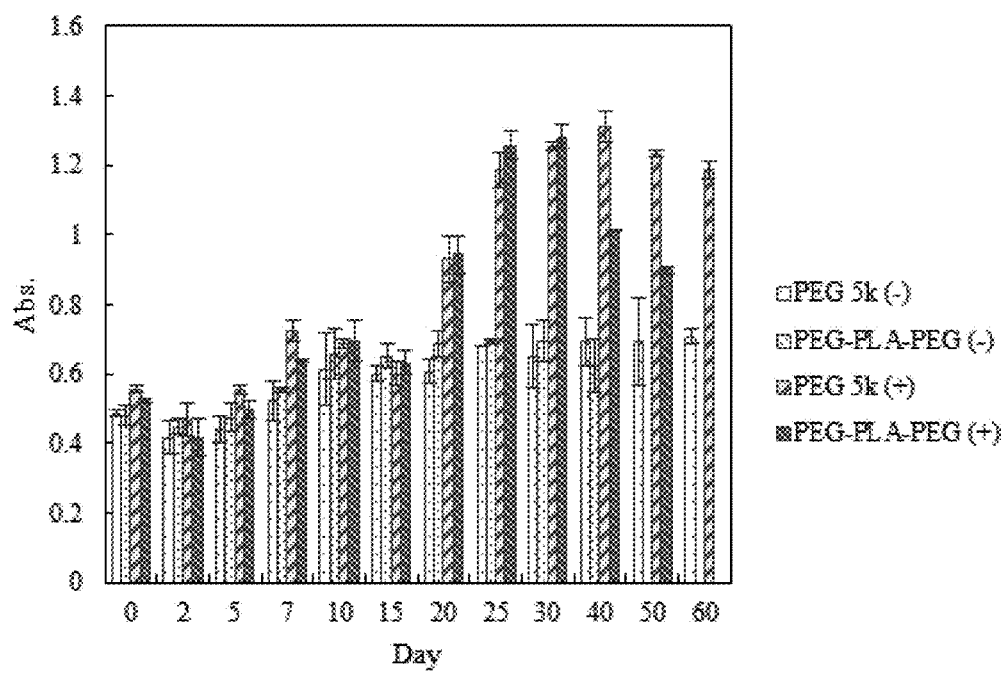
FIG. 16 indicates mitochondrial activity of various hydrogels as determined by MTT assay.

(4) Following centrifugation (1,500 rpm, 5 minutes), the supernatant was added to a 96-well plate at 100 μL/well followed by measuring absorbance at 570 nm (FIG. 16).

Mitochondrial activity as determined with the MTT assay decreased in all of the hydrogels during the early stage of culturing. Subsequently, although activity remained low in gel not mixed with RADA, a remarkable increase in activity was observed in gel mixed with RADA. This is thought to be due to an improvement in cell activity as a result of the peptide fiber structure mimicking the environment in the body. In addition, cell activity improved significantly in the case of using PEG-PLA-PEG. This is thought to be due to the effect of imparting degradability. In addition, a decrease in activity was confirmed during the latter stage of culturing in the case of using PEG-PLA-PEG. This suggests that the gel degraded and released cells.

Dimethylmethylene Blue (DMMB) Assay (1) 4 mg of DMMB were dissolved in 1.25 mL of ethanol followed by the addition of 0.75 mL of formic acid and 6.4 mL of a 1.0 M NaOH solution and bringing to a final volume of 250 mL with Milli-Q water to prepare a DMMB solution.

(2) The DMMB solution was added to a 96-well plate at 125 μL/well.

(3) A calibration curve working solution of chondroitin sulfate solution (in PBS) and sample (melted gel diluted two-fold with medium) were accurately pipetted into each well at 20 μL/well.

Figure 17:
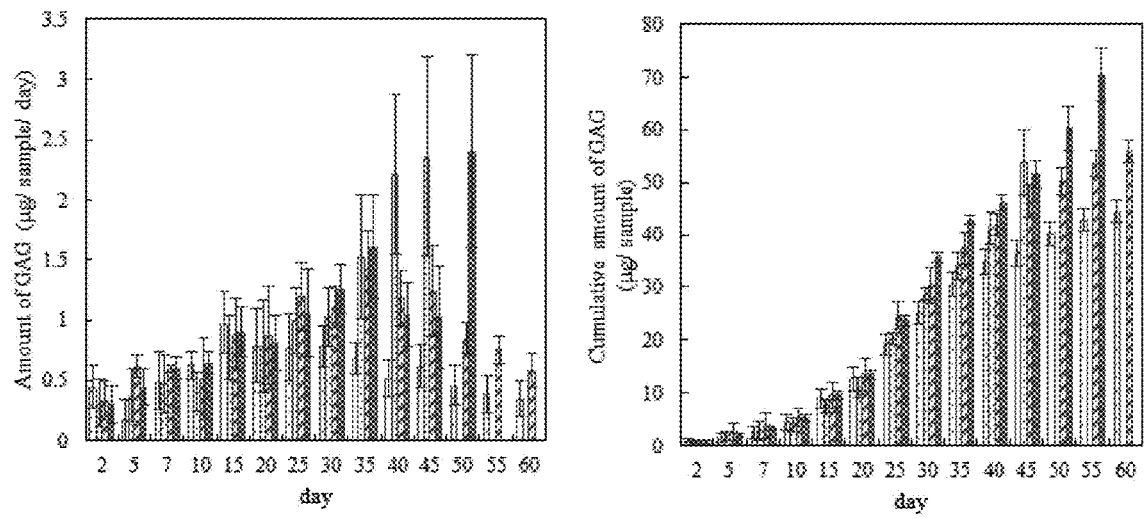
FIG. 17 indicates GAG production levels (left: amount of GAG produced per day, right: cumulative amount of GAG produced).
Figure 18:
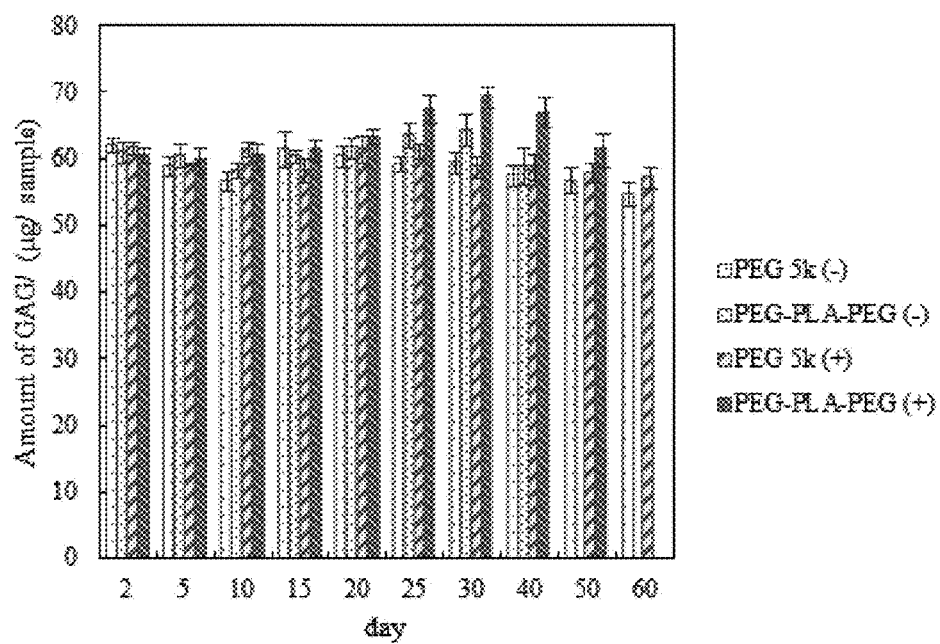
FIG. 18 indicates GAG production levels in gels.
Figure 19:
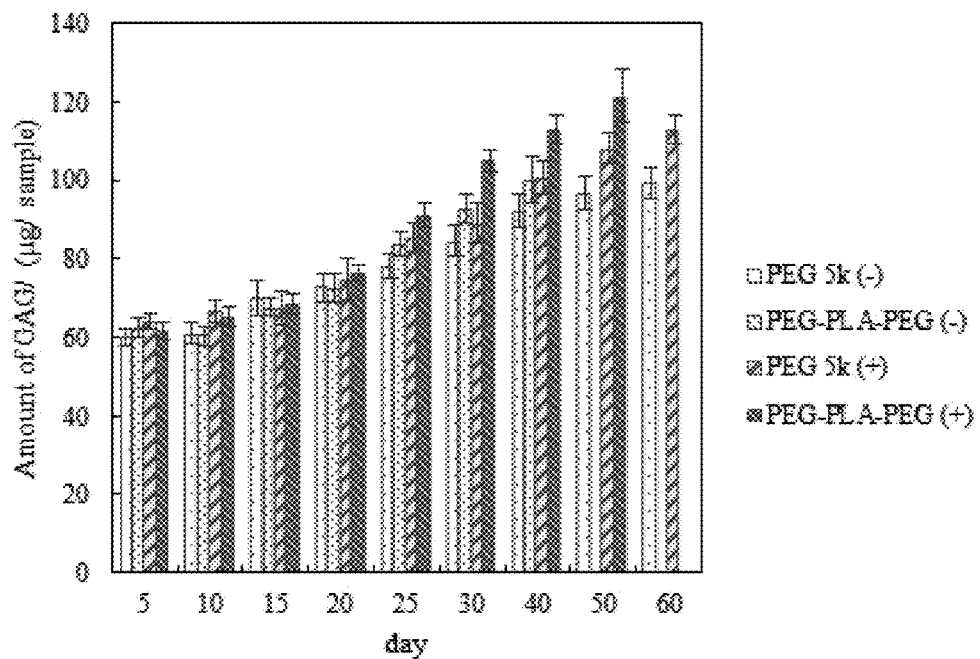
FIG. 19 indicates cumulative GAG production levels (in medium and gel).

(4) Absorbance at 570 nm was measured (FIGS. 17 to 19).

When the prepared chitosan/PEG-PLA-PEG/RADA16 gel was compared with the chitosan/PEG 5k/RADA16 gel, although the amount of GAG produced in the medium and the amount GAG produced in the gel indicated roughly the same levels of GAG production during the early stage of culturing, in the latter stage of culturing, the amount of GAG produced by the chitosan/PEG-PLA-PEG/RADA16 gel was higher. The chitosan/PEG-PLA-PEG/RADA16 gel was confirmed to demonstrate gradual degradation behavior under the culturing conditions, and GAG production is thought to have improved as a result of imparting degradability to the gel.

A polymerization initiator or polymerization stimulator (such as UV light or gamma rays and the like) is required in the case of using PEG-PLA-PEG having polymerizable functional groups on both ends (polymerizable functional group-PEG-PLA-PEG-polymerizable functional group) or in the case of using as a crosslinking material for gelation.

In this case, there are considerable disadvantages, such as (1) a considerable decrease in cell viability following the gelation reaction due to phototoxicity or a toxic signal such as a polymerization initiator degradation product, or (2) difficulty in ensuring safety at the clinical stage due to increased risk to cells of genetic abnormalities or malignant transformation attributable to irradiation with light (and mainly ultraviolet light) (Williams, et al., Biomaterials, 2005, 26, 1211-1218; Liu, et al., Adv. Mater., 2014, 26, 3912-3917; Cui, et al., Biomacromolecules, 2013, 14, 1904-1912).

On the other hand, succinimide-PEG-PLA-PEG-succinimide differs from physically crosslinked gels using PEG-PLA-PEG or PLA-PEG-PLA in that it is able to crosslink at extremely low temperatures. Thus, since it can be handled as a cell mixture having low viscoelasticity, it can be used as an injectable gel administered to the body, and therefore is highly compatible with clinical treatment.

In addition, since the reaction between protein molecule amino acid residues and succinimides having safe degradation products (by-products) is used as the driving force behind the gelation reaction, and since gelation proceeds simply by mixing, another third stimulating factor is not required.

As a result, the reaction has extremely low toxicity that enables cell viability following the gelation reaction to be maintained at 100% relative to prior to crosslinking.

INDUSTRIAL APPLICABILITY

The triblock copolymer of the present invention is extremely useful for the production of a biodegradable interpenetrating polymer network (IPN).

The invention claimed is:

1. A biodegradable injectable gel, comprising:
the triblock copolymer having a polyethylene glycol-poly(D,L-lactide)-polyethylene glycol skeleton, comprising a repeating unit represented by Formula I:

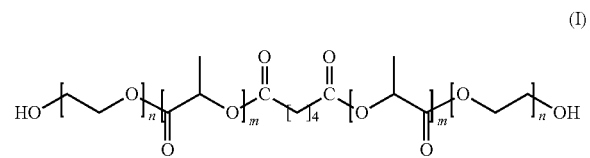

wherein n is 10 to 1000, and m is 2 to 100, chitosan, and a self-assembling peptide.

2. The biodegradable injectable gel according to claim 1, wherein the self-assembling peptide is (RADA)$_4$.

3. A crosslinking agent comprising Formula I:

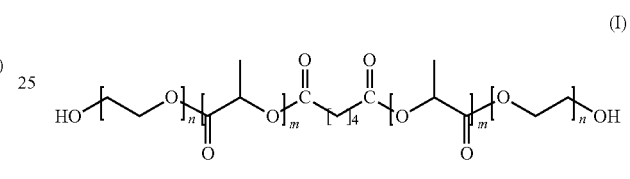

wherein n is 10 to 1000, and m is 2 to 100.

* * * * *